United States Patent

Mantegani et al.

[11] Patent Number: 6,087,371
[45] Date of Patent: Jul. 11, 2000

[54] HETEROCYCLYL-ERGOLINE DERIVATIVES AS 5-$HT_{1A}$ RECEPTOR LIGANDS

[75] Inventors: Sergio Mantegani, Milan; Tiziano Bandiera, Gambolò Pavia; Maurizio Meroni; Mario Varasi, both of Milan; Carla Caccia, Varese, all of Italy

[73] Assignee: Pharmacia & Upjohn S.p.A., Milan, Italy

[21] Appl. No.: 09/125,108

[22] PCT Filed: Feb. 7, 1997

[86] PCT No.: PCT/EP97/00582

§ 371 Date: Aug. 17, 1998

§ 102(e) Date: Aug. 17, 1998

[87] PCT Pub. No.: WO97/30050

PCT Pub. Date: Aug. 21, 1997

[30] Foreign Application Priority Data

Feb. 15, 1996 [GB] United Kingdom ............... 9603226

[51] Int. Cl.⁷ ............... A61K 37/437; C07D 457/00; C07D 471/04
[52] U.S. Cl. ............... 514/286; 546/67; 546/68
[58] Field of Search ............... 546/67, 68; 514/286

[56] References Cited

U.S. PATENT DOCUMENTS

| | | | |
|---|---|---|---|
| 4,785,001 | 11/1988 | Temperilli et al. | 514/288 |
| 4,839,363 | 6/1989 | Brambilla et al. | 514/288 |
| 4,847,253 | 7/1989 | Buonamici et al. | 514/253 |
| 4,859,678 | 8/1989 | Mantegani et al. | 514/269 |
| 5,210,194 | 5/1993 | Mantegani et al. | 544/361 |
| 5,430,001 | 7/1995 | Tomotsu et al. | 502/113 |

FOREIGN PATENT DOCUMENTS

| | | |
|---|---|---|
| 0 070 562 | 1/1983 | European Pat. Off. . |
| 0 128 479 | 12/1984 | European Pat. Off. . |
| 2 375 230 | 7/1978 | France . |
| 2 177 090 | 1/1987 | United Kingdom . |

*Primary Examiner*—Alan L. Rotman
*Attorney, Agent, or Firm*—Oblon, Spivak. McClelland, Maier & Neustadt, P.C.

[57] ABSTRACT

Ergoline derivative having formula (I) wherein $R_1$ is hydrogen atom or $C_{1-4}$ alkyl group; $R_2$ is hydrogen, chlorine, or bromine atom, methyl or $C_{1-4}$ alkylthio group; n is 0, 1 or 2; the substituent at position 8 is in α or β configuration; Het represents an aromatic 5-membered heterocyclic ring, said ring having three heteroatoms which are the same or different and which are selected from the group consisting of sulfur, oxygen and nitrogen atom and X is hydrogen, chlorine or bromine or fluorine atom, or a pharmaceutically acceptable acid addition salt thereof are active at the Central Nervous System level. A process for their preparation is also described, as are pharmaceutical compositions containing them.

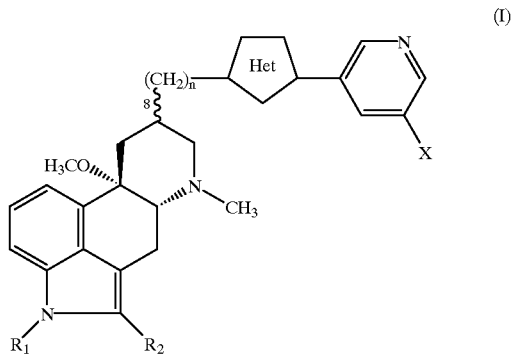

8 Claims, No Drawings

HETEROCYCLYL-ERGOLINE DERIVATIVES AS 5-HT$_{1A}$ RECEPTOR LIGANDS

This application claims priority from British Patent Application No. 9603226.3, the contents of which are incorporated herein by reference.

This invention relates to new heterocyclic-ergoline derivatives, to a process for their preparation, to their use as medicaments and to a pharmaceutical composition containing them.

The novel compounds act upon the central nervous system by binding to 5-HT$_{1A}$ receptors and hence can be used for the management of central nervous system pathologies. The said compounds can be employed for the treatment of various disorders associated with serotoninergic disfunctions, such as impairment of thermoregulation, memory function, sleep disorders, satiety control (i.e. food and beverage consumption), drugs addiction, control of drug withdrawal, hypertension, hyperemesis, depression, anxiety, psychosis and ischemic insult.

More particularly, the present invention relates to compounds of formula I:

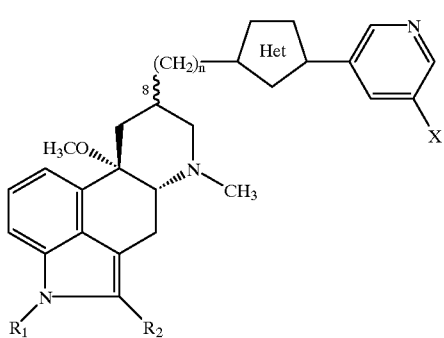

wherein

R$_1$ is hydrogen atom or C$_{1-4}$ alkyl group; R$_2$ is hydrogen, chlorine, or bromine atom, methyl or C$_{1-4}$ alkylthio group; n is 0, 1 or 2;

the substituent at position 8 is in α or β configuration;

Het represents an aromatic 5-membered heterocyclic ring, said ring having three heteroatoms which are the same or different and which are selected from the group consisting of sulfur, oxygen and nitrogen atom and X is hydrogen, chlorine or bromine or fluorine atom, or a pharmaceutically acceptable acid addition salt thereof.

The invention also provides a pharmaceutical formulation comprising a compound of formula I or suitable pharmaceutically acceptable acid addition salts including salts with both organic and inorganic acids in combination with a pharmaceutically acceptable excipient.

In the present specification, the term C$_{1-4}$ alkyl includes methyl, ethyl, propyl, isopropyl, n-butyl and tertbutyl groups.

The aromatic 5-membered heterocyclic ring in particular contains one or more nitrogen atoms and up to one sulphur or one oxygen atom but not together.

Preferably, these 5-membered heterocyclic rings include oxadiazole, thiadiazole, triazole which are linked to the ergolinyl and pyridinyl residues through the carbon atoms as illustrated below:

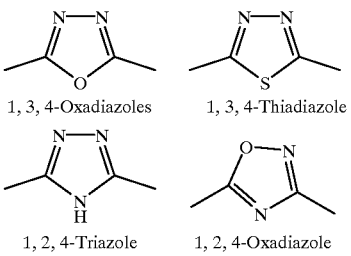

1,3,4-Oxadiazoles   1,3,4-Thiadiazole 1,2,4-Triazole   1,2,4-Oxadiazole

Pharmaceutically acceptable acids, which may be used in the acid addition salt formation, include maleic, citric, tartaric, fumaric, methane sulphonic, acetic, benzoic, succinic, gluconic, lactic, malic, mucoic, glutammic, ascorbic as organic acids or hydrochloric, hydrobromic, sulphuric or phosphoric as inorganic acids.

Among the addition salts obtained by employing acids hydrochloric, sulphoric, methanesulphoric, citric and succinic salts are the most preferred.

The compounds of formula I may be prepared using as starting material an appropriate derivative of the carboxylic function at position 8 of the ergoline framework and a suitable 3-substituted pyridine via well-known reactions of heterocyclic chemistry for obtaining penta-atomic heterocyclic rings having three heteroatoms.

The present invention also provides a process for the preparation the compounds of formula I or the acid addition salts thereof, which process comprises:

(i) reacting an activated derivative of a compound of formula II

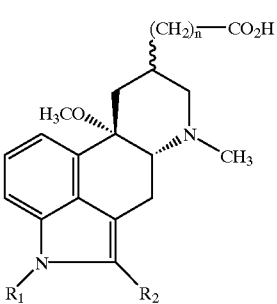

wherein R$_1$, R$_2$ and n are as above defined with a compound of formula III

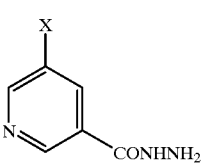

wherein X is as defined above; or (i') reacting the compound of the formula II as defined above with hydrazine hydrate and then reacting the resultant hydrazide derivative with a compound of formula III'

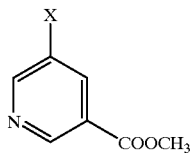  III' wherein X is as above defined;

(ii) reacting the resultant compound of formula IV

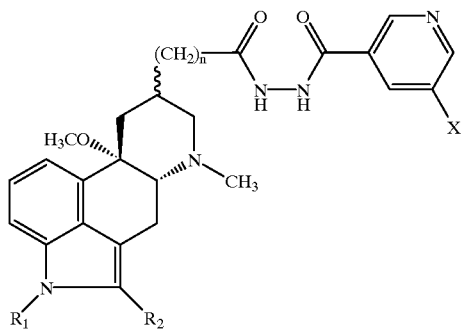  IV wherein $R_1$, $R_2$, n and X are as defined above, with a dehydrating agent, affording a compound of formula I wherein Het represents a group of the formula

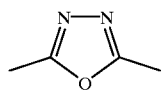

or (ii') reacting the resultant compound of formula IV with a sulphurating agent such as $P_2S_5$ or the like affording a compound of the formula I wherein Het represents a group of formula

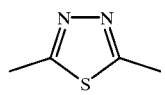

or (i'') reacting an activated derivative of a compound of the formula II as defined above with a compound of formula III''

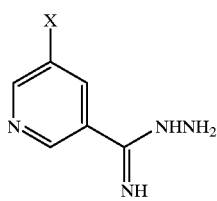  III'' wherein X is as defined above to afford a compound of formula I, wherein Het represents a group of the formula

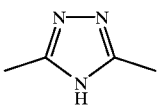

or (i''') reacting a compound of formula V

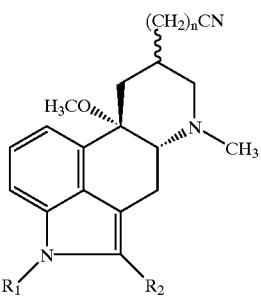  V wherein $R_1$, $R_2$ and n are as defined above, with hydroxylamine hydrochloride in the presence of a base and (ii''') reacting the resultant compound of formula VI:

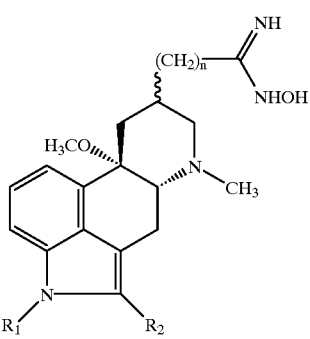  VI wherein n, $R_1$ and $R_2$ are as above defined, with a compound of formula III' as above defined to afford a compound of formula I wherein Het represents a group of formula

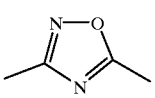

or (i$^{iv}$) reacting a compound of the formula VII

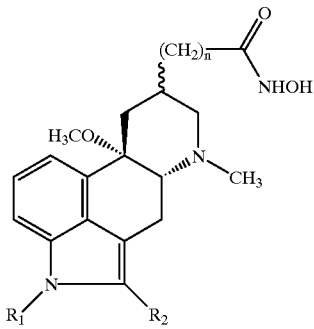

wherein n, $R_1$ and $R_2$ are as above defined with a compound of formula III$^{iV}$

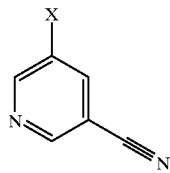

wherein X is as defined above to afford a compound of formula I wherein Het represents a group of formula

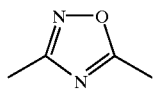

or
(i') reacting a compound of formula VIII

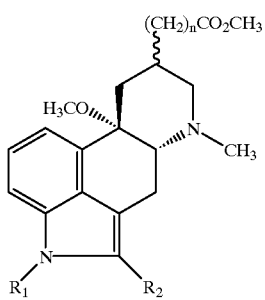

wherein $R_1$, $R_2$ and n are as defined above with a compound of formula III$^V$

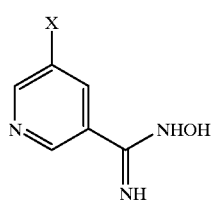

wherein X is as defined above to afford a compound of formula I wherein Het represents a group of formula

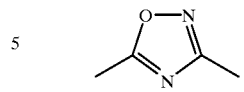

or
(i$^{vi}$) reacting a compound of the formula V as above defined with a compound of formula III$^{vi}$

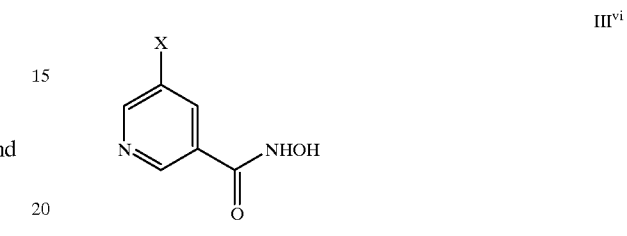

wherein X is as above defined, to afford a compound of formula I wherein Het represents a group of formula

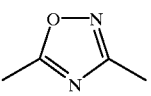

The compounds of formula I wherein $R_1$ is $C_{1-4}$ alkyl group, may be obtained from the corresponding compounds of formula I wherein $R_1$ is hydrogen by appropriate alkylation.

A compound of formula I wherein $R_2$ is hydrogen may be converted into another of the formula I wherein $R_2$ is chlorine, bromine or a $C_{1-4}$ alkylthio group by suitable reactions.

The activated derivatives of a compound of formula II include a compound of the formula II$_A$

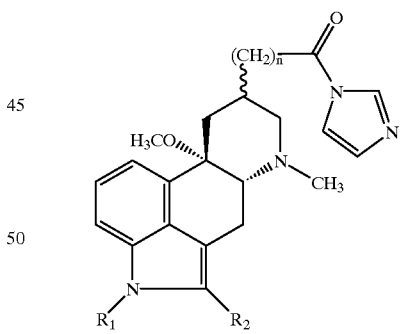

wherein $R_1$, $R_2$ and n are as defined above, which is obtained by reacting a compound of the formula II as above defined with 1,1' carbonyldimidazole.

Pharmaceutically acceptable acid addition salts of the compounds of formula I are obtained by appropriate treatment of the compound of the formula I with the desired acid.

Process step (i) is generally carried out by direct addition of a compound of formula III to a freshly prepared solution of an activated derivative of a compound of formula II and then refluxed from 1 to 5 hours.

The compound of formula IV is generally recovered by removing the solvent followed by a crystallization from ethanol or methanol.

Process step (ii) is conveniently carried out by reaction of a compound of formula IV with a dehydrating agent such as phosphorous pentachloride or trifluoroacetic anhydride or poliphosphoric acid in a solvent such as toluene or pyridine at reflux or preferably employing trimethylsilylpoliphosphate in refluxing toluene.

Process step (ii") is generally carried out by by reaction of a compound of formula IV with phosphorous pentasulfide in refluxing pyridine or with Lawesson's reagent [2,4-bis(4-methoxyphenyl)-1,3-dithia-2,4-diphosphetane-2,4-disulfide] in refluxing toluene.

The compounds of the present invention have been found to display interesting affinity for $5\text{-HT}_{1A}$ receptor in the brain with much less affinity for other receptors in particular $D_1$ and $D_2$ and $5\text{-HT}_2$ receptors.

Process step (i") is generally accomplished by reaction of an activated derivative of a compound of formula II with a compound of formula III" in refluxing ethanol in the presence of one equivalent of sodium methoxyde or ethoxyde.

Process step (i''') is carried out by reaction of a compound of formula V with hydroxylamine hydrochloride and one equivalent of sodium ethoxyde in refluxing ethanol. When the convertion into a compound of formula VI is concluded, the following step (ii''') is carried out by addition of a compound of formula III' and one equivalent of sodium ethoxyde and refluxing the reaction mixture from 4 to 15 hours.

The same methodology is employed for the reaction of a compound of formula VII (easily available by reaction of an activated derivative of a compound of formula II with hydroxylamine hydrochloride in pyridine at 50–100° C.) with a compound of formula $III^{iv}$.

Process step (i') is generally accomplished by reaction of a compound of formula VIII (easily available by reaction of an activated derivative of a compound of formula II with methanol at reflux) with a compound of formula $III^v$ in presence of one equivalent of sodium ethoxyde in refluxing ethanol.

The same methodology is employed in the reaction between a compound of formula V and a compound of formula $III^{vi}$.

The N-alkylation of a compound of formula I wherein $R^1$ is hydrogen may be carried out in accordance with the known methodologies for the N-alkylation of indoles, employing a compound of formula $R'_1$—Z wherein $R'_1$ is $C_{1-4}$ alkyl and Z is a leaving group such as chlorine, bromine, iodine. The reaction is conveniently carried out in an inert solvent such as dimethylsulphoxide and in presence of a strong base such as potassium or sodium hydroxide at a temperature ranging from 10 25 to 35° C.

The chlorination, bromination or thioalkylation of a compound of formula I wherein $R_2$ is hydrogen may also be carried out in accordance with the known methodologies, using standard chlorinating agents or brominating agents such as N—Cl or N—Br succinimide or sulphurylchloride or $C_{1-4}$ alkylsulphenylchloride.

The reaction is conveniently carried out in an inert solvent such as chloroform, methylene chloride or tetrahydrofuran at a temperature ranging from −5 to 30° C.

An activated derivative of a compound of formula II may be obtained by reaction of a compound of formula II with a small excess of N,N'-carbonyldiimidazole in a solvent such as tetrahydrofuran or 1,4-dioxane at a temperature ranging from 25 to 50° C. until complete dissolution of the starting acid.

The starting compounds of the formulae II, III, III', $III^{ii}$, $III^{iv}$, $III^v$, $III^{vi}$, V are known compounds or may be prepared according to well known methodologies.

The compounds of the present invention have been found to display interesting affinity for $5\text{-HT}_{1A}$ receptor in the brain with much less affinity for other receptors in particular $D_1$ and $D_2$ receptors.

The compounds of the present invention can find use on the management of anxiety, depression, schizophrenia and pain (Pharmacology and Toxicology 1989, 64, p.3–5, Drug of the future 1988, 13 (5), p 429–437, J. Neural Transm. 1988, 74, p.195–198), for the treatment of stress (Neuropharmac, 1989, 25,(5), p.471–476), allevation of the drug withdrawal (abstinence syndrome) due to the suppression of benzodiazepines, cocaine, alcohol and nicotine, or modification of the food intake and sexual behaviour (J.Receptor Research, 1988,8, p. 59–81), and to alleviate the neuronal damage following cerebral ischemia, acting as neuroprotectant agents (Stroke 1990, 21 (IV) p. 161; J.Cereb. Blood Flow Metabol. 1991, 11(II), p. 426; Pharmacology of cerebral ischemia, 1990, Stuttgart 1990, p.493–497)

The following biological examples illustrate the binding profile of the compounds of general formula I.

EXAMPLE a

Affinity for serotonin 1A ($5\text{-HT}_{1A}$) receptor [$^3$H-8-Hydroxy-2-dipropylaminotetralin ($^3$H-8-OH-DPAT)binding test]

Preparation of crude synaptosome fraction and binding assay were conducted in accordance with the method reported in Journal of Neurochemistry, vol 44, page 1685, 1985 by Hall et al. Freezed hippocampus dissected out from rats were homogenized in 40 volumes of ice cold 50 mM Tris-HCl buffer (pH. 7.4) and the suspension was centrifuged at 500× g for 10 minutes at 0° C.

The supernatant was centrifuged at 40,000× g for 20 minutes at 0° C. and the resulting pellet was homogenized in 40 volumes of the above buffer and incubated at 37° C. for 10 minutes. After completion of reaction, the suspension was centrifuged at 40,000× g for 20 minutes at 0° C. The resulting pellet was washed twice by resuspension in 40 volumes of the above buffer and centrifugation, and finally suspended in 60 volumes of ice-cold 50 mM Tris-HCl buffer (pH 7.4) containing 1 mM manganese chloride for use in the next assay.

To the aliquots (900 ml) of synaptosome membranes solution were added 50 ml of tritiated 8-OH-DPAT solution at the terminal concentration of 0.2 nM and 50 ml of test compound solution or 50 ml of its medium, and incubated at 37° C. for 10 minutes. Then to the mixture was added 5 ml of ice-cold 50 mM Tris-HCl buffer (pH 7.4) rapidly vacuum-filtered through Whatman$^R$ GF/B filters and washed twice with 5 ml of the same buffer. The radioactivity of the residue remaining on the filters was measured by liquid scintillation counter. Nonspecific binding was determined under the presence of $10^{-5}$M serotonin (5-HT). 50% Inhibition concentration ($IC_{50}$) of the test compound was graphically determined. The results are summarized in the table.

EXAMPLE b

Affinity for serotonin 2($5\text{-HT}_2$)receptor ($^3$H-Ketanserin binding test).

Preparation of crude synaptosome fraction and binding assay were conducted according to the method reported in Molecular Pharmacology, vol.21, page 301, 1981 by Leysen et al. Freezed cerebral cortex dissected out from rats were homogenized in 30 volumes of ice-cold 0.32M sucrose solution and the suspension was centrifuged at 1000× g for 10 minutes at 0° C. The supernatant was centrifuged at 40,000× g for 20 minutes at 0° C. and the resulting pellets was homogenized in 30 volumes of ice-cold 50 mM Tris- HCl buffer (pH.7.7) and incubated at 37° C. for 10 minutes. The suspension was centrifuged at 40,000× g for 20 minutes at 0° C. again. The resulting pellet was homogenized in 100 volumes of the above buffer and provided as synaptosome membranes solution for the next assay.

To the aliquots (900 m) of synaptosome membranes solution were added 50 ml solution of $^3$H-Ketanserin solution at the terminal concentration of 0.2 mM and 50 ml of test compound or its medium, and incubated at 37° C. for 20 minutes. After completion of the reaction, the mixture was rapidly vacuum-filtered through Whatman$^R$ GF/B filters. The filters were washed three times with 5 ml of the above buffer, and then the radioactivity of the residue remaining on the filters was measured by liquid scintillation counter. Non specific binding was determined under the presence of 10 mM of mianserin. 50% Inhibition concentration ($IC_{50}$) of the test compound was graphically determined. The results are summarized in the Table.

EXAMPLE c

Affinity for dopamine 2 ($D_2$)receptor ($^3$H-Spiperone binding test.)

Preparation of crude synaptosome fraction and binding assays were conducted in accordance with the method reported in European Journal of Pharmacology, vol 46, page 377,1977 by I.Creese et al. Freezed corpus striatum dissected out from rats were homogenized in 100 volumes of ice cold 50 mM Tris-HCl buffer (pH.7.7) and the suspension was centrifuged at 500× g for 10 minutes at 0° C.

The supernatant was centrifuged at 50,000× g for 15 minutes at 0° C. and the resulting pellet was homogenized in 100 volumes of the above buffer and then the suspension was centrifuged at 50,000× g for 15 minutes at 0° C. again. The resulting pellet was homogenized in 150 volumes of 50 mM Tris-HCl buffer (PH 7.1) containing 120 mM potassium chloride, 2 mM calcium chloride, 1 mM magnesium chloride, 0,1 ascorbic acid and 10 mM pargyline. The suspension was incubated at 37° C. for 10 minutes and then provided as synaptosome membranes solution for the next assays. To the aliquots (900 m) of synaptosome membranes solution were added 50 ml of H-Spiperone solution at the terminal concentration of 0.2 nM and 50 ml of test compound solution or 50 ml of its medium, and incubated at 37° C. for 20 minutes. After completion of the reaction, the mixture was rapidly vacuum-filtered through Whatman$^R$ GF/B filters. The filters were washed three times with 5 ml of the above buffer, and then the radioactivity of the residue remaining on the filters was measured by liquid scintillation counter. Nonspecific binding was determined under presence of 100 mM of L)-Sulpiride 50% Inhibition concentration ($IC_{50}$) of the test compound was graphically determined.

The results are summarized in the Table:

| Compound prepared in | $D_1$ | $D_2$ | 5-$HT_{1A}$ | 5-$HT_2$ |
| --- | --- | --- | --- | --- |
| Example 2 | 1.12 | 3.64 | 0.2 | 2.4 |
| Example 4 | 1.4 | 2.93 | 0.3 | 3.4 |
| Example 8 | 2.04 | 1.95 | 0.009 | 0.027 |
| Example 10 | 2.48 | 2.51 | 0.011 | 0.89 |

Affinity expressed as $IC_{50}$ μM

Moreover, the compounds of formula I were unexpectely found to be able to modulate the PKC translocation in synaptosomes of different brain area such as hippocampus and striatum.

The compounds of the present invention could be therefore employed in the treatment of pathologies associated with a reduced functionality of the PKC signal transduction pathway such as various forms of dementia, memory disturbances, Alzheimer's disease and Down's syndrome.

PKC translocation in different brain's area

Purified synaptosomes have been obtained following the procedure described by Dunkley (Dunkley P. R., Health J. W:, Harrison S. M., Jarvie P. E., Glenfield P. J. and Rostas J. A. P.

A rapid percolation gradient procedure for isolation of synaptosomes directly from Si fraction: homogeneity and morphology of subcellular fractions. Brain res 441:59–71, 1988).

Synaptosomes purified from cortex, hippocampus were incubated (10 mg/ml) for 15 min at 30° C. in presence of increasing doses of the compounds of the present invention dissolved in tartaric acid (pH 7.0) or of the vehicle alone.

After incubation, purified synaptosomes were collected in cold Krebs buffer containing 10 mM EGTA and then processed according to Shearmann et al (Shearman M. S., Shinomura T., Oda T. and Nishizuka Y. Protein kinase C subspecies in adult rat hippocampal synaptosomes. Activation by diacylglycerol and arachidonic acid. FEBS Lett 279:261–264, 1991).

Synaptosomes have been lysed in this solution for 30 min at 4° C. with stirring. The lysed suspension was centrifuged at 100000 g for 60 min. The resultant supernatant was processed as "cytosolic fraction". The pellet was again resuspended in lysis buffer containing 0.1% Triton X-100 at 4° C. for 45 min. The centrifugation step was repeated and the resulting supernatant represents the "membrane fraction". Proteins present in the cytosolic and membrane fractions were separated by SDS-PAGE and blotted on nitrocellulose paper.

PKC on Western blots was detected with a polyclonal total PKC antibody (Upstate Biotechnology). Western blot analysis of PKC isozymes has been performed utilizing monoclonal antibodies (GIBCO). Antigen antibody complexes were detected by enhanced chemiluminescence. Results have been analysed by computer assisted Image analysis and expressed as per cent of PKC translocation in control conditions.

Data of the PKC translocation in hippocampal synaptosomes of compound of the invention are shown in the following table:

| | |
| --- | --- |
| CONTROL | 100 |
| COMPOUND PREPARED IN EXAMPLE 4 | 126 |

In a physiological assay using purified and viable synaptosomes, the compounds of the invention are able to increase the translocation of PKC to the membrane compartment. These results are of particular interest considering that the concentration of PKC is significantly reduced in the particulate fraction of various regions of Alzheimer's disease brain) Masliah E., Cole G., Shimohama S., Hansen L., De Teresa R., Terry R. D. and Saitoh T. Differential involvement of protein kinase C isozymes in Alzheimer's disease. J Neurosci 10:2113–2124, 1990).

The toxicity of the compounds of the present invention is quite negligible, and they are therefore safely employable as useful drugs.

A patient is treated according to the present invention by a method comprising the administering to the patient an effective amount of a compound of formula I or a pharmaceutically acceptable salt thereof. In this way a compound of formula I or its pharmaceutically acceptable salt can be used to control conditions attributable to serotoninergic disfunctions such as the impairment of thermoregulation or memory function, sleep disorders, drug addiction, hypertension, hyperemesis, depression, anxiety or psychosis, or the control of satiety or drug withdrawal, cerebral ischemia.

The invention further provides a pharmaceutical composition comprising an ergoline derivative having the general formula I or a pharmaceutically acceptable salt thereof in admixture with pharmaceutically acceptable diluent or carrier.

Compounds of formula I and their salts described herein may be administered by parenteral or oral route, preferably by oral route. Depending on administration route, the compositions may be in the form of solid, semi-soild or liquid dosage form, such as, for example, tablets, pils, capsules, powders, liquids, suspension, or the like. The composition will include a conventional pharmaceutical carrier, adjuvants, etc.

The dosage of the present drugs varies in accordance with the sex, age, condition or medical records of the patients, as well as according to the route or the purpose of the administration.

In general, the drugs may be administered as singler doses or as divided doses so as to provide, say, about 1–10 mg/kg body weight per day of effective ingredients, preferably about 0.1–5 mg/kg body weight.

The pharmaceutical compositions containing the compounds of the invention are prepared according to conventional methods with the usual ingredients.

Thus, for oral administration, the pharmaceutical compositions containing the compounds of the invention are preferably tablets, pills or capsules which contain the active substance together with diluents, such as, for instance, lactose, dextrose, sucrose, mannitol, sorbitol, sucrose, cellulose, lubricants, for example, silica, talc, stearic acid, magnesium or calcium stearate and or polyethylenglycols; or they may also contain binders, such as, for example, starches, gelatine, methyl-cellulose, gum arabic, tragacanth, polyvinylpyrrolidone, disintegrating agents, such as, for instance, starches, alginic acid, alginates; effervescing mixture; dyestuff; sweeteners, wetting agents, such as, for instance, lecithin, polysorbates, laurylsulphates, and in general non-toxic and pharmacologically inactive substances used in pharmaceutical formulations.

Said pharmaceutical preparations may be manufactured in known manner, for instance, by mean of mixing, granulating, tabletting, sugar-coating, or film-coating processes.

Also the said pharmaceutical formulations containing the compounds of the invention may be prepared by known methods and they can be, for example, syrup or drops or tablets for the oral administration, sterile solution for injection, or suppositories.

A tablet formulation may be prepared as follow:

|  | QUANTITY (mg/tablet) |
|---|---|
| ACTIVE INGREDIENT | 25 |
| STARCH DRIED | 425 |
| MAGNESIUM STEARATE | 10 |
| TOTAL | 460 |

The above ingredients are blended together and compressed to form tablets each weighting 460 mg.

The following examples illustrate the preparation of the compound of the invention.

EXAMPLE 1

6-Methyl-8β-methyl-[5-(5-bromo-pyridin-3-yl)-1,2,4-oxadiazol-3-yl]-10α-methoxy-ergoline To a solution of 5.5 g of 6-methyl-8β-cyanomethyl-10α-methoxy-ergoline in ml 100 of anhydrous ethanol was added 1.55 g of hydroxylamine hydrochloride followed by a freshly prepared solution of 0.52 g of sodium in ml 25 of anhydrous ethanol.

After stirring 1 hour at room temperature, the precipitated (NaCl) was filtered off and the resulting solution was refluxed for 10 hours.

The solution was then concentrated to ml 35 and further added of 8.9 g of 3-methoxycarbonyl-5-bromo-pyridine and a freshly prepared solution of 1.1 g of sodium in ml 10 of anhydrous ethanol.

The resulting solution was refluxed for 5 hours. The solvent was removed and the residue chromatographed on silica gel eluting with ethylacetate/cyclohexane 1/1.

After evaporation of the solvent and crystallization from a small volume of acetone, 2.7 g of te title compound were obtained, m.p.195–198° C.

EXAMPLE 2

1,6-Dimethyl-8β-methyl-[5-(5-bromo-pyridin-3-yl)-1,2,4-oxadiazol-3-yl]-10α-methoxy-ergoline To a stirred solution of 2 g of 6-methyl-8β-methyl-[5-(5-bromo-pyridin-3-yl)-1,2,4-oxadiazol-3-yl]-10α-methoxy-ergoline in ml 30 of dimethylsulphoxide was added at room temperature, 0.5 g of finely ground sodium hydroxyde. After stirring for 30 mins., a solution of 0.9 g of methyl iodide in m 10 of dimethylsulphoxide was added and the stirring was continued for 1 hour.

The resulting reaction mixture was diluted with ethylacetate and throrougly washed with brine.

After drying, the solvent was removed and the residue chromatographed on silica gel eluting with ethylacetate/cyclohexane ⅓,to give the title compound in 65% yield, m.p.176–179° C.

EXAMPLE 3

6-Methyl-8β-methyl-[3-(5-bromo-pyridin-3-yl)-1,2,4-oxadiazol-5-yl]-10α-methoxy-ergoline To a stirred solution of 4 g of 6-methyl-8β-cyanomethyl-10α-methoxy-ergoline in ml 50 of anhydrous ethanol were added 5.6 g of 5-bromo-nicotinoylhydroxamic acid and a freshly prepared solution of 0.65 g of sodium in ml 15 of anhydrous ethanol. The resulting solution was refluxed for 24 hours, then the solvent was removed and the residue columned on silica gel eluting with acetone/cyclohexane ¼.

The fraction containing the product were pooled and the solvent removed to afford after crystallization from ethanol 1.7 g of the title compound, m.p.201–206° C.

EXAMPLE 4

1,6-Dimethyl-8β-methyl-[3-(5-bromo-pyridin-3-yl)-1,2,4-oxadiazol-5-yl]-10α-methoxy-ergoline Operating as in Example 2, but employing 6-methyl-8β-methyl-[3-(5-bromo-pyridin-3-yl)-1,2,4-oxadiazol-5-yl]-10α-methoxy-ergoline instead of 6-methyl-80-methyl-[5-(5-bromo-pyridin-3 -yl)-1,2,4-oxadiazol-3-yl]-10α-methoxy-ergoline, the title compound was obtained in 55% yield, m.p.185–189° C.

EXAMPLE 5
1,6-Dimethyl-2-bromo-8β-methyl-[3-(5-bromo-pyridin-3-yl)-1,2,4-oxadiazol-5-yl]-10α-methoxy-ergoline To a solution of 2 g of 1,6-dimethyl-8β-methyl-[3-(5-bromo-pyridin-3-yl)-1,2,4-oxadiazol-5-yl]-10α-methoxy-ergoline in 75 ml of dioxane were added portionwise 0.9 g of N-bromo-succinimide. After stirring at 40° C. for 2 hours, the solvent was removed and the residue was chromatographed on silica gel eluting with ethylacetate.

After crystallization from isopropanol 1.3 g of the title compound were obtained, m.p.167–172° C.

EXAMPLE 6
1,6-Dimethyl-2-chloro-8β-methyl-[3-(5-bromo-pyridin-3-yl)-1,2,4-oxadiazol-5-yl]-10α-methoxy-ergoline To a stirred solution of 2 g of 1,6-dimethyl-8β-methyl[3-(5-bromo-pyridin-3-yl)-1,2,4-oxadiazol-5-yl]-10α-methoxy-ergoline in ml 50 of acetonitrile and ml 0.5 of BF3-2 Et2O was added dropwise a solution of 0.6 g of sulphuryichloride ($SO_2Cl_2$) in ml 15 of acetonitrile at −5° C.

The stirring was continued for 1 hour, then the solution was diluted with ethylacetate and washed with 1 M ammonium hydroxyde solution.

After drying, the solvent was removed and the residue twice crystallized from acetone, to give 0.8 g of the title compound, m.p.159–164° C.

EXAMPLE 7
6-Methyl-8β-[2-(5-bromo-pyridin-3-yl)-1,3,4-oxadiazol-5-yl]-10α-methoxy-ergoline To a stirred solution of 12 g of 6-methyl-8β-carboxy-10α-methoxy-ergoline in ml 150 of tetrahydrofuran was added portionwise 7.2 g of 1,1'-carbonyldiimidazole then heated at 50° C. for 15 mins.

To the clear solution was added 8.5 g of 5-bromo-nicotinoylhydrazide and the cloudy mixture was heated at reflux for 3 hours.

The solvent was removed and the residue crystallized from methanol affording 12.3 g of N-(6-methyl-8β-carbonyl-10α-methoxy-ergoline)-N'-(5-bromo-nicotinoyl)-hydrazine, m.p.214–217° C.

A stirred sospension of 3 g of N-(6-methyl-8β-carbonyl-10α-methoxy-ergoline)-N'-(5-bromo-nicotinoyl)-hydrazine in ml 100 of toluene was treated with 10 g of trimethylsilylpoliphosphate then refluxed for 15 hours.

The cloudy solution was washed with 1 M sodium hydroxide solution then with brine.

After drying and evaporation of the solvent, the residue was chromatographed on silica gel eluting with ethylacetate.

Crystallization from ethanol, afforded 0.8 g of the title compound, m.p.155–157° C.

EXAMPLE 8
1,6-Dimethyl-8β-[2-(5-bromo-pyridin-3-yl)-1,3,4-oxadiazol-5-yl]-10α-methoxy-ergoline Operating as in Example 2, but employing 6-methyl-B-[β-(5-bromo-pyridin-3-yl)-1,3,4-oxadiazol-5-yl]-10α-methoxy-ergoline instead of 6-methyl-8β-methyl[5-(5-bromo-pyridin-3-yl)-1,2,4-oxadiazol-3-yl]-10α-methoxy-ergoline, the title compound was obtained in 35% yield, m.p.183–186° C.

EXAMPLE 9
6-Methyl-8β-methyl-[2-(5-bromo-Pyridin-3-yl)-1,3,4-oxadiazol-5-yl]-10α-methoxy-ergoline Operating as in Example 7, but employing 6-methyl-8β-carboxymethyl-10α-methoxy-ergoline, instead of 6-methyl-8β-carboxy-10α-methoxy-ergoline, the title compound was obtained in 27% yield, m.p.196–198° C.

EXAMPLE 10
1,6-Dimethyl-8β-methyl-[2-(5-bromo-pyridin-3-yl)-1,3,4-oxadiazol-5-yl]-10α-methoxy-ergoline Operating as in Example 2, but employing 6-methyl-8β-methyl-[2-(5-bromo-pyridin-3-yl)-1,3,4-oxadiazol-5-yl]-10α-methoxy-ergoline instead of 6-methyl-8β-methyl-[5-(5-bromo-pyridin-3-yl)-1,2,4-oxadiazol-3-yl]-10α-methoxy-ergoline, the title compound was obtained in 35% yield, m.p.171–174° C.

EXAMPLE 11
6-Methyl-8β-[5-(5-bromo-pyridin-3-yl)-1,3,4-thiadiazol-5-yl]-10α-methoxy-ergoline To a stirred solution of 3.5 g of N-(6-methyl-8β-carbonyl-10α-methoxy-ergoline)-N'-(5-bromo-nicotinoyl)-hydrazine in ml 100 of pyidine was added 5 g of phosphorouspentasulfide. The yellow suspension was refluxed for 15 hours, then cooled at room temperature and treated with ml 100 of 5 M ammonium hydroxyde solution. After stririring for 2 hours, the resulting green solution was diluted with ethylacetate and washed with brine.

After drying and removal of the solvent, the residue was filtered on a small pad on silica gel eluting with acetone/cyclohexane ½ to afford 1.2 g of the title compound, m.p.157–163° C.

EXAMPLE 12
6-Methyl-8β-methyl-[2-(5-bromo-pyridin-3-yl)-1,3,4-oxadiazol-5-yl]-10α-methoxy-ergoline Operating as in Example 7, but employing 6-methyl-8α-carboxymethyl-10α-methoxy-ergoline, instead of 6-methyl-8β-carboxy-10α-methoxy-ergoline, the title compound was obtained in 15% yield, m.p.143–147° C.

EXAMPLE 13
6-Methyl-8β-[2-(5-bromo-pyridin-3-yl)-1,2,4-triazol-5-yl]-10α-methoxy-ergoline To a stirred solution of 5 g of 6-methyl-8β-carboxy-10α-methoxy-ergoline in ml 100 of 1,4-dioxane was added portionwise 2.9 g of 1,1'-diimidazole-carbonyl then heating at 50° C. for 15 mins.

To the clear solution was added 6 g of 5-bromo-nicotinoylhydrazidine and 0.8 g of freshly prepared sodium ethoxide, then the cloudy mixture was heated at reflux for 10 hours.

The solvent was removed and the residue taken up in ethylacetate was washed with brine.

After drying, the solvent was removed and the crude reaction mixture was columned on silica gel eluting with ethylacetate/cyclohexane ⅓ yielding after crytallization from acetone 1.8 g of the title compound, m.p.178–131° C.

EXAMPLE 14
6-Methyl-8β-methyl-[2-(5-bromo-pyridin-3-yl)-1,3,4-triazol-5-yl]-10α-methoxy-ergoline Operating as in Example 12, but employing 6-methyl-8β-carboxymethyl-10α-methoxy-ergoline instead of 6-methyl-8β-carboxy-10α-methoxy-ergoline, the title compound was obtained in 17% yield, m.p.163–168° C.

EXAMPLE 15
6-Methyl-8β-[2-(5-bromo-pyridin-3-yl)-1,3,4-triazol-5-yl]-10α-methoxy-ergoline Operating as in Example 12, but employing 6-methyl-8β-carboxy-10α-methoxy-ergoline instead of 6-methyl-8β-carboxy-10α-methoxy-ergoline, the title compound was obtained in 23% yield, m.p.142–146° C.

EXAMPLE 16

1,6-Dimethyl-8β-[5-(5-bromo-pyridin-3-yl)-1,3,4-thiadiazol-5-yl]-10α-methoxy-ergoline Operating as in Example 2, but employing 6-methyl-8β-[5-(5-bromo-pyridin-3-yl)-1,3,4-thiadiazol-5-yl]-10α-methoxy-ergoline instead 6-methyl-8β-methy-[5-(5-bromo-pyridin-3-yl)-1,2,4-oxadiazol-3-yl]-10α-methoxy-ergoline, the title compound was obtained in 35% yield, m.p.131–137° C.

What is claimed is:

1. An ergoline derivative of the formula I

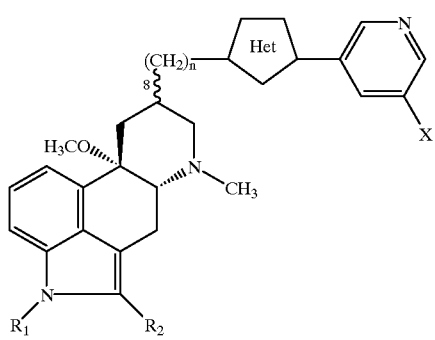

wherein $R_1$ is hydrogen or $C_{1-4}$ alkyl; $R_2$ is hydrogen, chlorine, bromine, methyl or $C_{1-4}$ alkylthio; n is 1 or 2; the substituent at position 8 is in the α or β configuration; the 5-membered heterocyclic ring represented by Het is an oxadiozole, thiadiazole or triazole group which is linked to the ergolinyl and pyridinyl groups through the carbon atoms as shown:

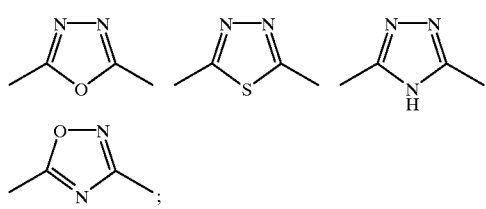

and X is hydrogen, chlorine, bromine or fluorine; or a pharmaceutically acceptable acid addition salt thereof.

2. A pharmaceutical composition comprising a pharmaceutically acceptable diluent or carrier and, as an active ingredient, a compound as claimed in claim 1.

3. A process for the preparation of a compound as defined in claim 1, the process comprising (i) reacting an activated derivative of a compound of formula II

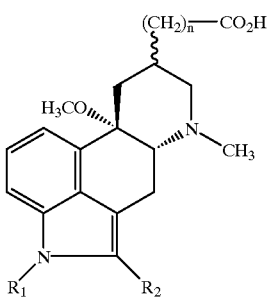

wherein $R_1$, $R_2$, and n are as defined in claim 1 with a compound of formula III

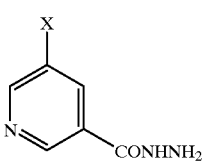

wherein X is as defined in claim 1; or (i″) reacting the compound of the formula II as defined above with hydrazine hydrate and then reacting the resultant hydrazide derivative with a compound of formula III'

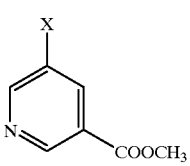

wherein X is as defined above defined;

(ii) reacting the resultant compound of formula IV

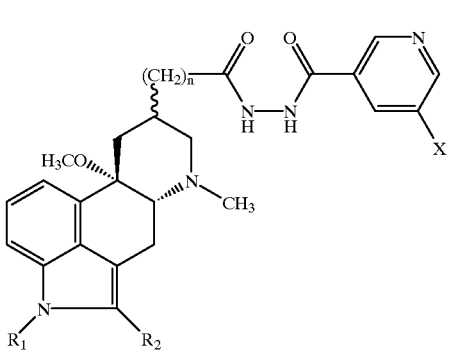

wherein $R_1$, $R_2$, n and X are as defined above, with a dehydrating agent, affording a compound of formula I wherein Het represents a group of the formula

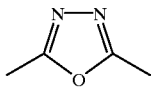

or (ii") reacting the resultant compound of formula IV as defined above with a sulphurating agent affording a compound of the formula I wherein Het represents a group of formula

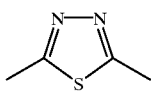

(i') reacting an activated derivative of a compound of the formula II as defined above with a compound of formula III"

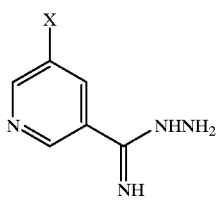

III"

wherein X is as defined above to afford a compound of formula I, wherein Het represents a group of the formula

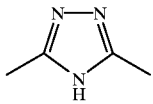

or ($i^{iv}$) reacting a compound of formula V

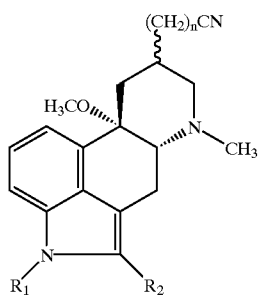

V wherein $R_1$, $R_2$ and n are as defined above, with hydroxylamine hydrochloride in the presence of a base and (ii''') reacting the resultant compound of formula VI:

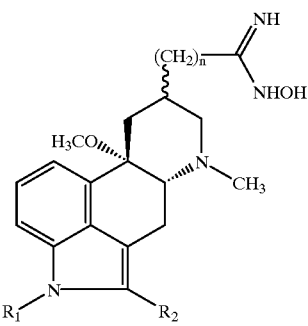

VI wherein n, $R_1$ and $R_2$ are as above defined, with a compound of formula III' as above defined to afford a compound of formula I wherein Het represents a group of formula

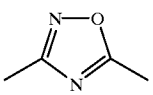

or (iv) reacting a compound of the formula VII

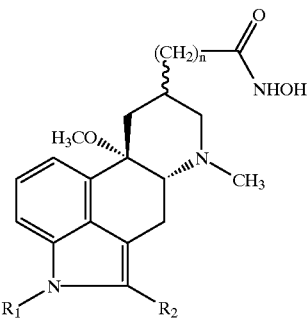

VII wherein n, $R_1$ and $R_2$ are as above defined with a compound of formula $III^{iv}$

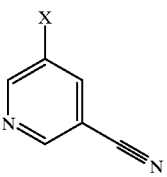

$III^{iv}$ wherein X is as defined above to afford a compound of formula I wherein Het represents a group of formula

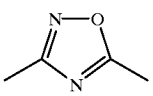

or (i') reacting a compound of formula VIII

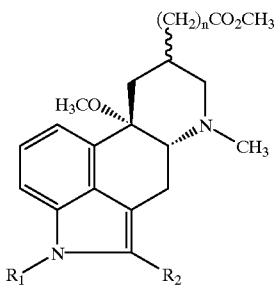

VIII wherein $R_1$, $R_2$ and n are as defined above with a compound of formula $III^V$

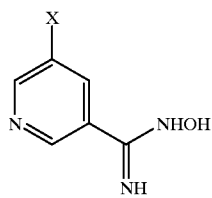

$III^v$ wherein X is as defined above to afford a compound of formula I wherein Het represents a group of formula

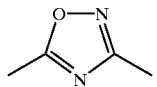

or (i'') reacting a compound of the formula V as above defined with a compound of formula $III^{vi}$

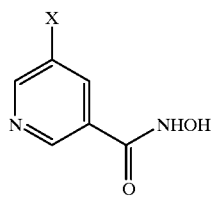

$III^{vi}$ wherein X is as above defined, to afford a compound of formula I wherein Het represents a group of formula

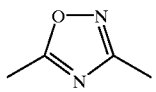

4. A process according to claim 3, which further comprises alkylating an ergoline derivative of formula I wherein $R_1$ is hydrogen to produce a derivative of formula I wherein $R_1$ is $C_{1-4}$ alkyl.

5. A process according to claim 3 which further comprises converting an ergoline derivative of formula I wherein $R_2$ is hydrogen into another of formula I wherein $R_2$ is chlorine, bromine or $C_{1-4}$ alkylthio.

6. A process according to claim 3 which further comprises treating an ergoline derivative of formula I with an acid to produce a pharmaceutically acceptable acid addition salt thereof.

7. A method of treating central nervous system pathologies which comprises administering to a subject a pharmaceutically acceptable amount of a compound of claim 1.

8. A method of treating a condition associated with serotoninergic disfunction which comprises administering to a patient in need thereof, a pharmaceutically acceptable amount of a compound of claim 1.

* * * * *